US009629753B2

(12) United States Patent
Golubovic et al.

(10) Patent No.: US 9,629,753 B2
(45) Date of Patent: Apr. 25, 2017

(54) DISPOSABLE PUSH-UP BRA LINER

(71) Applicants: Milan Golubovic, Astoria, NY (US); Marko Golubovic, Woodbridge, NJ (US)

(72) Inventors: Milan Golubovic, Astoria, NY (US); Marko Golubovic, Woodbridge, NJ (US)

(*) Notice: Subject to any disclaimer, the term of this patent is extended or adjusted under 35 U.S.C. 154(b) by 0 days.

(21) Appl. No.: 14/094,181

(22) Filed: Dec. 2, 2013

(65) Prior Publication Data

US 2014/0302745 A1  Oct. 9, 2014

Related U.S. Application Data

(60) Provisional application No. 61/830,986, filed on Jun. 4, 2013.

(51) Int. Cl.
*A41C 3/00* (2006.01)
*A61F 13/15* (2006.01)
*A61F 13/14* (2006.01)

(52) U.S. Cl.
CPC ............ *A61F 13/15* (2013.01); *A61F 13/145* (2013.01); *A61F 2013/15016* (2013.01)

(58) Field of Classification Search
CPC ........... A41C 3/00; A41C 3/0064; A41C 3/04; A41C 3/10; A41C 3/12; A41C 3/14; A41C 3/142; A41C 3/146
USPC ..... 450/37, 38, 54–57; 2/53–56, 59, 58, 267
See application file for complete search history.

(56) References Cited

U.S. PATENT DOCUMENTS

| | | | | |
|---|---|---|---|---|
| 4,747,162 | A | | 5/1988 | Yanagihara |
| 5,603,653 | A | * | 2/1997 | Hartman ......................... 450/56 |
| 5,664,984 | A | * | 9/1997 | Laughridge .................... 450/57 |
| 5,716,255 | A | * | 2/1998 | Abercrombie et al. ........ 450/60 |
| 5,980,359 | A | * | 11/1999 | Brown ............................. 450/57 |
| 6,138,276 | A | | 10/2000 | Asciutto et al. |
| 6,203,399 | B1 | | 3/2001 | Hackney |
| 6,341,377 | B1 | * | 1/2002 | Faries et al. ......................... 2/53 |
| 7,794,304 | B2 | * | 9/2010 | Frye ............................... 450/37 |
| 7,905,763 | B1 | * | 3/2011 | Frank ............................. 450/37 |
| 8,075,367 | B2 | * | 12/2011 | Taylor ............................ 450/37 |
| 8,246,416 | B2 | * | 8/2012 | Frye ............................... 450/37 |
| 2006/0252344 | A1 | | 11/2006 | Jian |

* cited by examiner

*Primary Examiner* — Gloria Hale
(74) *Attorney, Agent, or Firm* — Global Intellectual Property Agency, LLC; Daniel Boudwin

(57) ABSTRACT

The present disposable push up bra liner consists of a pair of bra cup pads and a center pad, each having an adhesive side for removably attaching said pad to a bra and an absorptive side composed of four separate layers. The present invention provides a novel and comfortable means for absorbing excessive perspiration around the bra line in order to avoid unsightly stains on the wearer's surrounding clothing and odors. The present invention is simple to use, easy to install, and may be freely disposed of at any point. The disposable bra liner further provides vertical support for a wearer's breasts, essentially converting any conventional bra into a push-up bra.

7 Claims, 4 Drawing Sheets

DISPOSABLE PUSH-UP BRA LINER

CROSS REFERENCE TO RELATED APPLICATION

This application claims the benefit of U.S. Provisional Application No. 61/830,986 filed on Jun. 4, 2013, entitled "Disposable Bra Liner." The above identified patent application is herein incorporated by reference in its entirety to provide continuity of disclosure.

BACKGROUND OF THE INVENTION

Field of the Invention

The present invention relates to perspiration absorption devices. More specifically, the present invention relates to disposable perspiration absorption liners adapted to fit within a bra and provide vertical support to a user's breasts.

Many women have a tendency to perspire around their bra line, especially when under stress, at work, or when performing physical activity. Excessive unwanted perspiration can result in embarrassing odors, sweat stains, or eventually discoloration of the surrounding clothes. Excessive perspiration can also lead to the need to constantly wash the affected bras, which increases the amount of wear and tear on those bras and thus requires that they be replaced more often. It can be expensive to have to constantly replace worn down bras, especially for women with a unique bra size who must specially order bras to fit their specific measurements.

Current inventions seek to address the problem of excessive bra line perspiration in a number of ways. Some inventions provide a single, elongated pad designed to be placed between the bra and the individual's breasts. This type of pad is often very uncomfortable, however, and can be difficult to properly place. Other types of perspiration-absorbent pads use straps or adhesives to keep the pad secured in position, but these can be uncomfortable to wear or, in the case of adhesives, leave a residue on the user's skin. Finally, antiperspirants are also available, but they are not one hundred percent effective compared to pads, which wick all of the perspiration that their volume can hold away from the body.

The present invention addresses all of the issues inherent to the prior devices designed to combat perspiration around the bra line, while also providing additional features. The present disposable push-up bra liner is extremely comfortable to wear, as it merely sits within the bra cup and is not an additional article that the user must strap, wrap, or otherwise attach to her body. The present invention is also easily secured to the bra because it is simply removably attached by the adhesive layer to the inside of the bra cup. The present disposable push-up bra liner also is specifically designed to target the areas where most of the perspiration along the bra line accumulates, thereby avoiding embarrassing stains from perspiration soaking through the woman's garment. Finally, the present invention provides an additional benefit not seen in the prior art of disposable bra liners in that it also provides a lifting or vertical support effect for the user's breasts. This feature is useful for women who wish to convert their conventional bra into a push-up bra, while simultaneously dealing with unsightly bra line perspiration.

Description of the Prior Art

Devices have been disclosed in the prior art that relate to perspiration absorption devices. These include devices that have been patented and published in patent application publications. These devices generally relate to pads or liners to absorb perspiration that fit under articles of clothing, over regions of the body that are most likely to produce perspiration. The following is a list of devices deemed most relevant to the present disclosure, which are herein described for the purposes of highlighting and differentiating the unique aspects of the present invention, and further highlighting the drawbacks existing in the prior art.

One such device is U.S. Pat. No. 4,747,162 to Yanagihara, which discloses a disposable perspiration absorption pad. Yanagihara has an adhesive layer adapted to be applied directly to the body and is designed to cover any portion of the body that the user wishes. Like the present invention, Yanagihara seeks to prevent embarrassing perspiration stains or discoloration from marring an individual's clothing, but the present is specifically designed to be placed within a bra, while also converting normal bras into push-up bras by adding vertical support to the user's breasts.

Another such device is U.S. Pat. No. 5,716,255 to Abercrombie, which discloses a disposable brassiere perspiration liner. Abercrombie comprises an elongated liner portion that extends underneath the breasts of the user and has a raised middle portion to capture additional perspiration between the breasts. The elongated liner portion is contoured to hold the user's breasts. The liner has an adhesive backside portion that is designed to removably adhere to the user's bra and hold the liner in position. The present invention is also a bra perspiration liner, but it is adapted to fit within the individual bra cups, rather than extending across the entire base of the bra. Furthermore, the present invention is designed to provide additional vertical support to breasts, essentially converting a normal bra to a push-up bra, which is a feature that Abercrombie lacks.

U.S. Pat. No. 6,138,276 to Asciutto discloses another such device, an underarm perspiration shield. Asciutto describes a perspiration-absorbing pad that has an attached strap that can fit over an individual's shoulder, positioning the pad over the individual's armpit. Like Asciutto, the present invention is specifically targeted to absorb perspiration from a specific area of the body. Unlike Asciutto, the present invention uses adhesive as the means of securing the liner in place, not a strap, and further is specifically adapted to fit within a bra cup, not around an armpit.

Another such device is U.S. Pat. No. 6,203,399 to Hackney, which discloses an elongated perspiration absorption pad that is adapted to be situated between the cups of a bra. Unlike Abercrombie, which has a raised middle portion to capture additional perspiration from the breasts, Hackney has a notch in the center of the elongated pad that allows the absorption pad to be ideally positioned between the cups of the bra. Even a well-positioned elongated pad is awkward and uncomfortable to wear, however. The present invention is more comfortable to wear because it comprises two or three separate components, depending upon the embodiment, which may independently be placed and ideally positioned for maximum comfort.

Finally, U.S. Pat. No. 6,341,377 to Faries discloses a perspiration-absorbing pad that has an absorbent layer and a gel layer that can adhere to skin. The absorbent layer can absorb perspiration and the gel layer closes skin pores that it comes into contact with, thereby preventing perspiration from forming in the area. The pad is designed to be placed between adjacent skin surfaces, such as under the breast. The present invention rests directly against the user's skin to absorb unwanted perspiration, unlike Faries. Furthermore, Faries is designed to be used independently of a bra or any other clothing, whereas the present invention is specifically designed to work in cooperation with a bra.

The present invention provides a new and unique perspiration-absorbent, disposable bra liner that is specifically designed to fit within a bra cup. The present disposable bra liner has an adhesive side for removably securing the pad within the bra cup and an absorbent side. The present liners may also have an adhesive wing that folds around the underwire of the bra as an additional means of securement. The present invention is also designed to be thicker in certain areas, providing vertical support to a woman's breasts as if she were wearing a push up bra. The present disposable bra liner substantially diverges in design elements from the prior art and consequently it is clear that there is a need in the art for an improvement to existing perspiration-absorbing devices. In this regard the instant invention substantially fulfills these needs.

SUMMARY OF THE INVENTION

In view of the foregoing disadvantages inherent in the known types of perspiration-absorbing devices now present in the prior art, the present invention provides a new disposable bra liner wherein the same can be utilized for providing convenience for the user when seeking to obtain relief from excessive breast perspiration.

It is therefore an object of the present invention to provide a new and improved disposable bra liner device that has all of the advantages of the prior art and none of the disadvantages.

It is another object of the present invention to provide a disposable bra liner that is easily replaceable and swappable.

Another object of the present invention is to provide a disposable bra liner that absorbs perspiration and keeps an individual's bra line dry.

Yet another object of the present invention is to provide a disposable bra liner that reduces the need to wash bras and reduces wear and tear on said bras.

Yet another object of the present invention is to provide a disposable bra liner that provides vertical support for a user's breasts.

Yet another object of the present invention is to provide a disposable bra liner that is comfortable to wear and that does not interfere with the normal workings of the user's bra.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
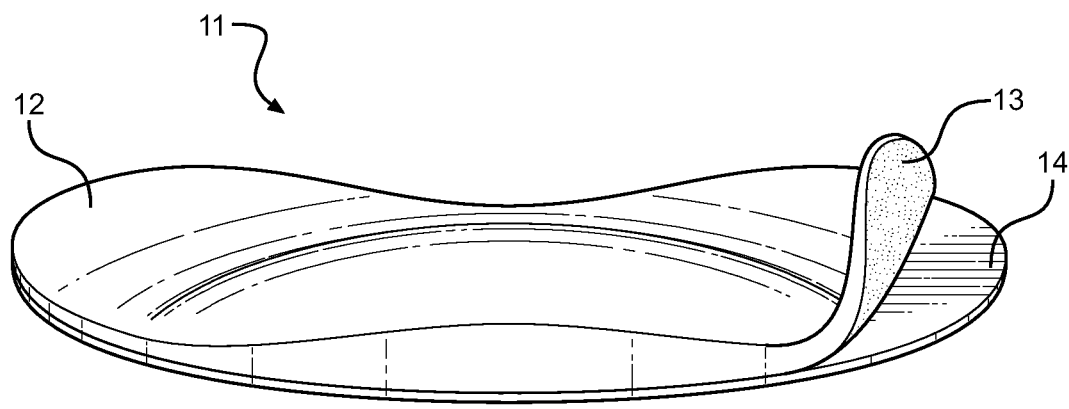
FIG. 1 shows a perspective view of the bra cup liner of the present invention being peeled off its backing, which protects the liner's adhesive layer.

Reference is made herein to the attached drawings. Like reference numerals are used throughout the drawings to depict like or similar elements of the disposable bra liner. For the purposes of presenting a brief and clear description of the present invention, the preferred embodiment will be discussed as used for placing the present liner within a bra to absorb perspiration and provide additional vertical support to the individual's breasts. The figures are intended for representative purposes only and should not be considered to be limiting in any respect.

The present disposable bra liner consists of a pair of bra cup liners and optionally a center liner affixed to the center strap of the bra, which lies over the woman's breastbone. The liners are designed to absorb perspiration around the bra line and store said perspiration and odor for easy disposal at a later time. The present disposable bra liners are designed to target the areas of greatest perspiration in the region and prevent that perspiration from creating embarrassing sweat stains or discoloration on the surrounding clothing. The liners can come in a variety of sizes and configurations designed to fit within all manner of bra sizes.

Referring now to FIG. 1, there is shown a perspective view of the bra cup liner of the present invention being peeled away from its backing. The present bra cup liner 11 consists of a pad composed of an absorptive portion 12 and an adhesive backside portion 13. The absorptive portion 12 is composed of four layers. The first layer comprises a porous, hydrophobic substance such as polyester or polypropylene. This is the layer that comes in contact with the user's skin and therefore must be simultaneously comfortable and allow moisture to pass through it and enter the deeper layers of the absorptive portion. The second layer comprises a textile or textile-like material with strong absorptive capabilities, such as air-laid paper. This is the first layer of the absorptive portion that is designed to absorb moisture. This layer is also provided to impart additional volume to the bra cup liner 11, thereby increasing the present invention ability to provide vertical support to users. The third and fourth layers of the absorptive portion comprise an ultra-absorbent gel and a superabsorbent polymer, respectively. The primary purpose of these layers is solely to absorb moisture wicked away from the user's skin.

The adhesive backside portion 13 is composed of any material known in the prior capable of removably, but securely, affixing the present invention within the bra. The adhesive backside portion 13 may be a layer of adhesive or a film placed along the backside of the first portion 12, and will preferably not leave a residue behind on the bra once it is removed. The adhesive backside portion 13 allows the present invention to self-secure within bra cups so it is easy to install and use. The backing 14 is provided against the exposed face of the adhesive backside portion 13 so that the adhesive backside portion 13 does not lose its adhesive properties during storage prior to use.

The bra cup liner 11 is provided in a roughly elliptical shape that has parallel, rounded concave and convex portions along its long edges. The bra cup liner 11 is adapted to fit within a bra cup, with its convex portion directed towards the user at the base of the bra cup and the concave portion directed towards the center of the bra cup. The bra cup liner 11 preferably has a slight curve upwards at its ends to track the curvature of a woman's breasts. The present bra cup liner 11 is thicker in its middle portion and tapers towards the ends to accommodate the fact that the majority of perspiration around the bra line is generated near the middle portion of the present bra cup liner 11. The overall thickness, size, and shape of the present invention can be adjusted for each bra size in order to maximize comfort for the user.

Optionally, the present invention may additionally have an adhesive wing structure extending from the bra cup liner adapted to wrap around the underwire of the bra and adhere to the bottom of the bra cup. The wing structure provides an additional means of securement for the bra cup liner 11 and at the same time provides cushioning material to cover the underwire of the bra, which can often be uncomfortable and dig into wearers' sides.

Figure 2A:
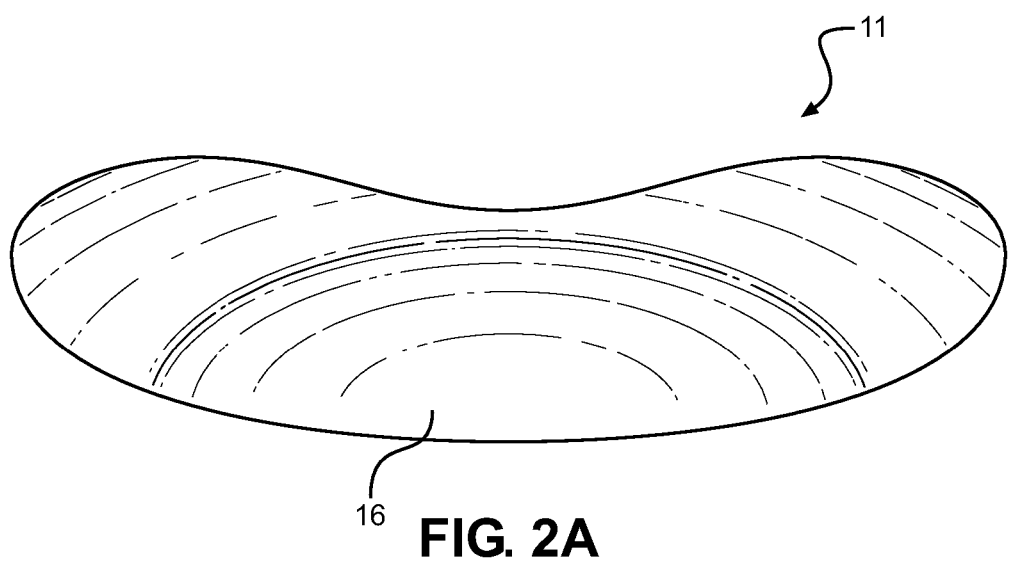
FIG. 2A shows a top-down view of the preferred embodiment of the bra cup liner portion of the present invention.
Figure 2B:
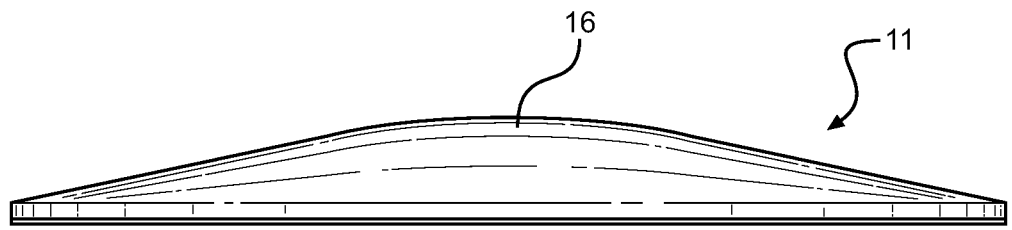
FIG. 2B shows a front view of the preferred embodiment of the bra cup liner present invention.
Figure 2C:
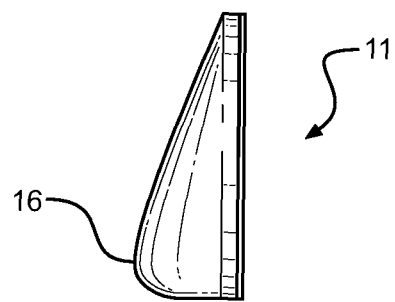
FIG. 2C shows a side view of the preferred embodiment of the bra cup liner of the present invention.

Referring now to FIGS. 2A, 2B, and 2C there are shown a top-down, a front, and a side view, respectively, of the preferred embodiment of the bra cup liner of the present invention. The bra cup liner 11 does not have a uniform thickness throughout, but rather is adapted to provide additional support in certain areas of a woman's breasts when in use. The depicted and preferred embodiment of the bra cup liner 11 of the present invention is thicker in the front and center, convex region of the device and gradually tapers outwardly towards the back, concave region and towards the sides of the device. This configuration creates a raised portion 16 in the front and center region of the bra cup liner 11 that is adapted to comfortably fit under and support the user's breasts. The raised portion 16 supports the user's breasts because it sits in the bra cup beneath the breasts, towards the user, which allows the raised portion 16 to vertically support the user's breasts as a whole. The varying thickness throughout the bra cup liner 11 can be variable depending upon the size of the bra that the bra liner is adapted to fit into in order to provide maximum support and comfort to the user.

Figure 3:
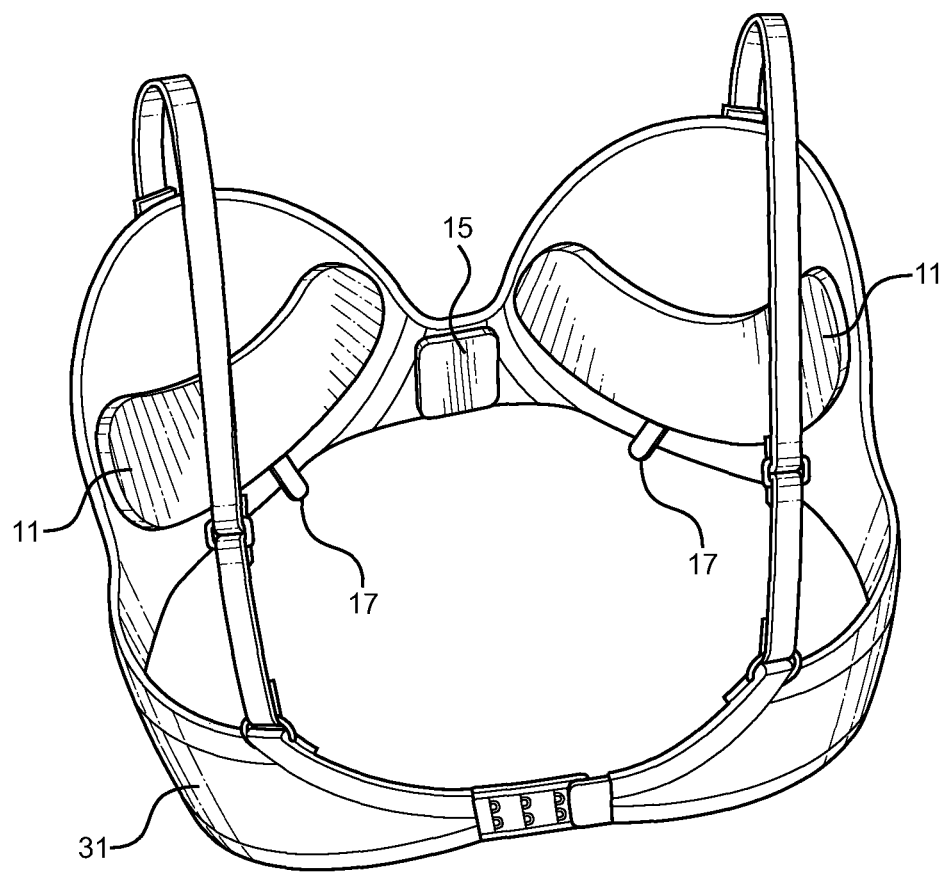
FIG. 3 shows a perspective view of the present invention as it appears when secured within a bra.

Referring now to FIG. 3, there is shown a perspective view of the preferred embodiment of the present invention secured within a bra. The preferred embodiment of the present invention includes a center liner 15, in addition to a pair of bra cup liners 11 as described above, that is removably affixed to the portion of the bra that connects the two bra cups and rests over the sternum of the user. The center liner 15 is composed of the same integrally connected adhesive and absorptive layers as the bra cup liners 11, but has a different size adapted to absorb sweat between the wearer's breasts, over her breastbone. The center liner 15 is depicted as roughly rectangular in shape, but can be of any size, shape, and thickness suitable for fitting between the wearer's breasts. Like the bra cup liners 11, the center liner 15 can be designed to be different sizes or shapes depending upon the bra size. The center liner 15 may also be provided with a backing in order to preserve its adhesive character until use.

The bra cup liners 11 are placed within the bra cups such that the thinner, concave portion of the bra cup liner 11 is facing towards the central portion of the bra cup and the convex portion of the bra cup liner 11 is facing the lower outer edge of the bra cup. The present invention is placed in this manner to situate the raised portion, which rests along the bottom edge of the bra cup liner 11, ideally beneath the user's breasts so that the raised portion may provide vertical support to the user's breasts, mimicking the effect of a push up bra.

Figure 4:
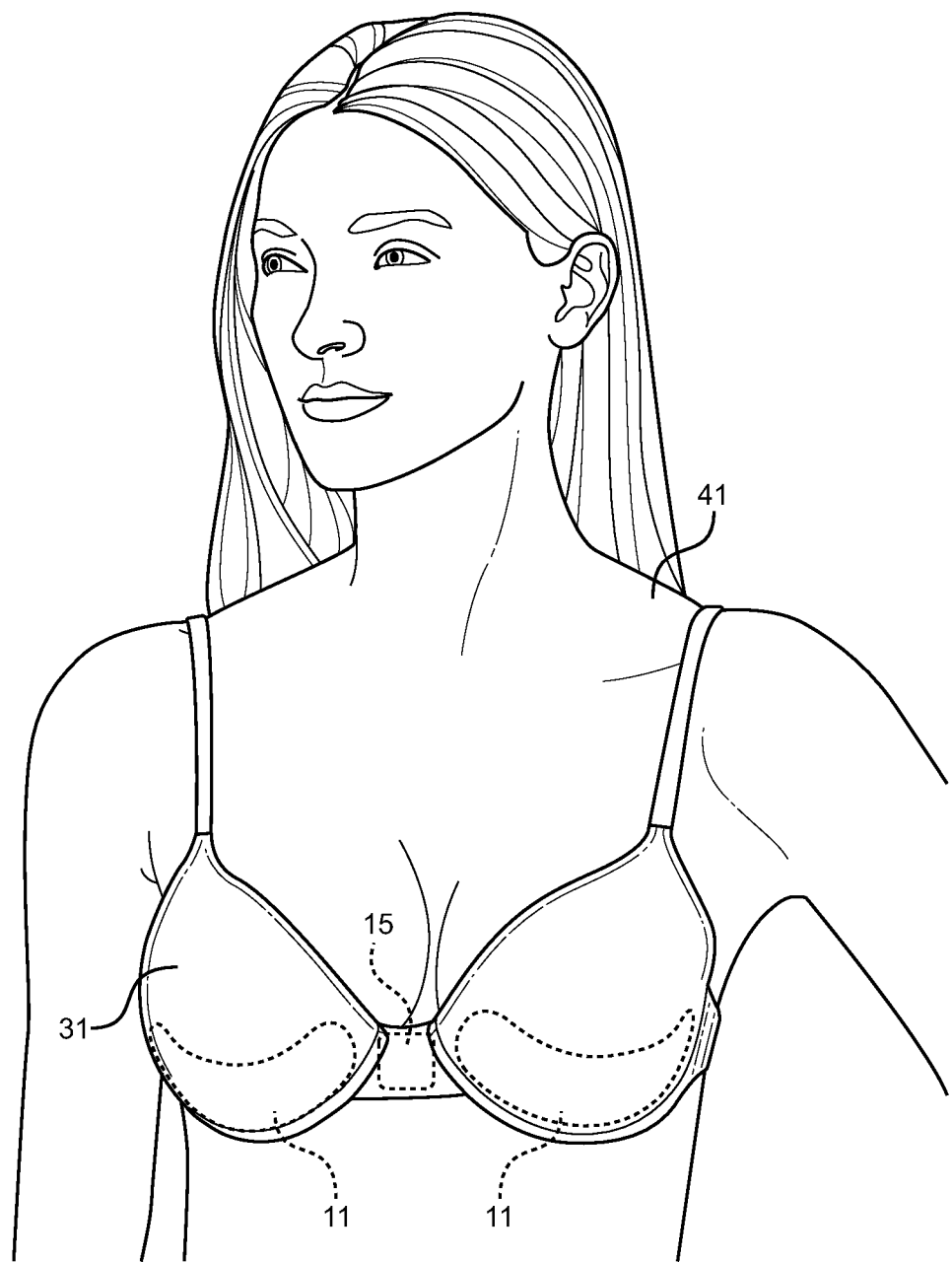
FIG. 4 shows a perspective view of the preferred embodiment of the present invention, as it appears when in use.

Referring now to FIG. 4, there is shown a perspective view of an alternate embodiment of the present invention, as it appears when worn by a user. The present disposable bra liner is adapted to provide additional vertical support to a wearer's breasts, acting to convert a conventional bra into a push-up bra. The present invention does so via the bra cup liners 11, which have sufficient thickness to push up a wearer's breasts and give her additional lift. The thick material of the bra cup liners 11 is absorptive, comfortable, and lifting.

The depicted and alternate embodiment of the present invention has a wing 17 disposed along the base of the bra cup liner 11. The wing 17 has an adhesive layer that wraps around the underside of the bra cup to provide an additional securement means, along with the adhesive backside portion of the bra cup liner 11, to ensure that the bra cup liner 11 stays in place. The adhesive backside portion of the wing 17 may, like the adhesive backside portion of the bra cup liner 11, comprise any material known in the prior capable of removably, but securely, affixing the present invention to the bra. The wing 17 may further be padded in order to provide the user some additional relief from the wires contained within the underside of the bra cup, which are often very uncomfortable for users.

Figure 5:
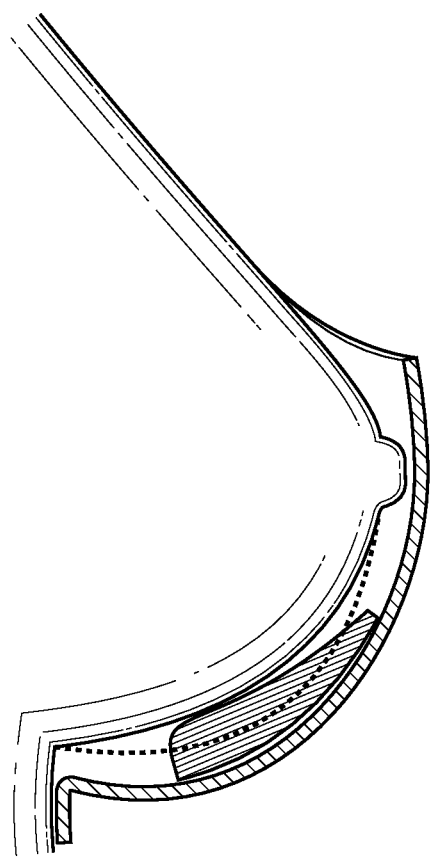
FIG. 5 shows a side cut-out view of the bra cup liner of the present invention, as it appears when in use.

Referring now to FIG. 5, there is shown a side cross-sectional view of the bra cup liner of the present invention, demonstrating how it provides vertical support to a user's breasts. The bra cup liner is affixed within the bra cup such that the thicker, raised portion is situated towards the user and beneath the user's breasts. The raised portion is then able to push up the user's breasts within the bra cup, mimicking the effects of a traditional push up bra. This additional vertical support characteristic of the present invention adds additional functionality to the traditional art of perspiration absorbing bra liners, making the present invention extremely useful for users who may wish to reversibly convert their bras into push up bras, while at the same time offering those users relief from bra line perspiration.

In use, an individual removes the backing from the adhesive layer of a pair of bra cup liners and optionally a center liner. The individual then places each of the bra cup liners on the bottom surface of a bra cup with the adhesive side down, towards the inside surface of the bra cup, and the absorptive side positioned such that it is underneath the wearer's breast. In this position the present disposable bra cup liner is ideally positioned to cover the areas of the wearer's bra line that perspire the most, namely the underside of the breasts. If the user wishes, she may then similarly remove the backing from the center liner and place it in position on the bra's center strap such that the adhesive backside portion keeps the liner secured to the bra strap and the absorptive layer is pointed inwardly towards the person. When all of the present bra liners are secured, the user may then put the bra on. The absorptive portion of the bra cup liners and the center liner are formed of four layers of material that are designed to wick away perspiration and other moisture from the user's skin, thereby keeping the user dry and preventing the user's perspiration from damaging or discoloring her bra or surrounding clothing. The present bra liner may then be disposed of at any point the user wishes.

Overall, the present disposable bra liner provides a novel device that combines the ability to absorb perspiration with the ability to provide lift and support to a wearer's breasts. This device provides women with the ability to avoid embarrassing stains or odors, while at the same time achieving the look that they want. Furthermore, the device is simple to install, easy to remove, and may be freely disposed of at the user's wish. Other such absorptive bra padding devices do not additionally provide vertical support to the user and often use uncomfortable means to secure the pads to the user, whereas the present invention instead secures the pads to the bra itself.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A bra perspiration absorption and support device, comprising:
    a bra cup liner adapted to rest within a bra cup and adapted to absorb perspiration, said bra cup liner comprising an absorptive portion and a backside adhesive portion;
    said backside adhesive portion comprising an adhesive adapted to removably attach said bra cup liner to a bra cup;
    said absorptive portion adapted to absorb moisture;
    said absorptive portion comprising a first layer comprising a porous hydrophobic substance, a second layer comprising an absorptive textile material, a third layer comprising an absorptive gel, and a fourth layer comprising a superabsorbent polymer;
    said absorptive portion comprising a raised central portion adapted to provide vertical support to a wearer's breasts.

2. The bra perspiration absorption and support device of claim 1, further comprising an adhesive tab attached to each of said bra cup liners, said adhesive tab comprising an adhesive layer adapted to be secured around a bottom portion of a bra underwire.

3. The bra perspiration absorption and support device of claim 1, wherein said raised central portion comprises a thicker region substantially in a middle, lower region of said bra cup liner, tapering outwardly therefrom to a periphery of said absorptive portion.

4. A bra perspiration absorption and support device, comprising:
    a bra center liner adapted to rest against a bra central connecting means, said bra center liner comprising an absorptive portion and a backside adhesive portion;
    said backside adhesive portion comprising an adhesive adapted to removably attach said bra center liner to said bra central connecting means;
    said absorptive portion adapted to absorb moisture;
    said absorptive portion comprising a first layer comprising a porous hydrophobic substance, a second layer comprising an absorptive textile material, a third layer comprising an absorptive gel, and a fourth layer comprising a superabsorbent polymer.

5. The bra perspiration absorption and support device of claim 4, further comprising an adhesive tab attached to said bra center liner, said adhesive tab comprising an adhesive layer adapted to be secured around a bottom portion of a bra underwire.

6. The bra perspiration absorption and support device of claim 4, wherein said raised central portion comprises a thicker region substantially in a middle, lower region of said bra center liner, tapering outwardly therefrom to a periphery of said absorptive portion.

7. A bra perspiration absorption and support device, comprising:
    a bra cup liner adapted to rest within a bra cup and adapted to absorb perspiration, said bra cup liner comprising an absorptive portion and a backside adhesive portion;
    said backside adhesive portion comprising an adhesive adapted to removably attach said bra cup liner to a bra cup;
    said absorptive portion adapted to absorb moisture and comprising a first layer comprising a porous hydrophobic substance, a second layer comprising an absorptive textile material, a third layer comprising an absorptive gel, and a fourth layer comprising a superabsorbent polymer;
    said absorptive portion comprising a raised central portion, said raised central portion comprising a thicker region substantially in a middle, lower region of said bra cup liner, tapering outwardly therefrom to a periphery of said absorptive portion and that is adapted to provide vertical support to a wearer's breasts;
    a bra center liner adapted to rest against a bra central connecting means, said bra center liner comprising a bra center absorptive portion and a bra center backside adhesive portion;
    said bra center liner backside adhesive portion comprising an adhesive adapted to removably attach said bra center liner to said bra central connecting means;
    said bra center liner absorptive portion adapted to absorb moisture and comprising a first layer comprising a porous hydrophobic substance, a second layer comprising an absorptive textile material, a third layer comprising an absorptive gel, and a fourth layer comprising a superabsorbent polymer;
    an adhesive tab attached to each of said bra center liner and said bra cup liner, said adhesive tab comprising an adhesive layer adapted to be secured around a bottom portion of a bra underwire.

* * * * *